United States Patent [19]

Sick

[11] 4,295,743

[45] Oct. 20, 1981

[54] APPARATUS FOR DETERMINING FAULTS IN STRIP MATERIAL

[75] Inventor: Erwin Sick, Icking, Fed. Rep. of Germany

[73] Assignee: Erwin Sick GmbH, Optik-Elektronik, Fed. Rep. of Germany

[21] Appl. No.: 49,534

[22] Filed: Jun. 18, 1979

[30] Foreign Application Priority Data

Jun. 23, 1978 [DE]  Fed. Rep. of Germany ....... 2827705

[51] Int. Cl.³ .............................................. G01B 11/30
[52] U.S. Cl. ..................................... 356/431; 250/572
[58] Field of Search ............... 356/429, 430, 431, 238; 250/563, 572

[56]  References Cited

U.S. PATENT DOCUMENTS

| 3,198,951 | 8/1965 | Lentze | 250/209 |
| 4,085,322 | 4/1978 | Sick | 356/431 |
| 4,116,527 | 9/1978 | Sick | 356/341 |

Primary Examiner—R. A. Rosenberger
Attorney, Agent, or Firm—Townsend and Townsend

[57] ABSTRACT

Apparatus for determining faults on strip material includes a scanning device for linewise scanning of a strip of material with a light beam, a first cylindrical lens extending parallel to the direction of the scanned lines and arranged to image the scanned line on a first cylindrical mirror with its focal line at right angles to the direction of the scanned lines.

Faults in the surface of the strip material such as dents, bumps and scratches give rise to characteristic deviations or deflection of the scanning light and the arrangement of the first cylindrical lens and first cylindrical mirror produce a convenient spatial distribution of the light in the image field of the first cylindrical mirror which can be detected by suitably disposed detectors to yield information about the nature and location of the fault. The apparatus includes various other optical components to produce a desired grouping of the deviated light beams to aid their identification and subsequent analysis. The apparatus can also operate with transmitted light. The particular arrangements shown are characterized by their compact arrangement.

18 Claims, 9 Drawing Figures

APPARATUS FOR DETERMINING FAULTS IN STRIP MATERIAL

The invention relates to an apparatus for determining faults on strip material and has particular reference to an apparatus in which a strip of material is scanned linewise by a bead of light and angular deviations of the light received from the strip both in a plane including the scanning line and transverse thereto are separately detected to indicate the nature of the fault.

It is known that such angular deviations i.e. deviations from the customarily expected direction or range of directions occurring with fault free material, are indications of the presence and nature of a fault therein.

The invention thus has especial relevance to the determination of faults of the kind which deflect a sharply defined light beam, in particular a laser beam incident under a predetermined angle, through specified angular amounts or in a specified range of solid angles.

Apparatuses for the determination of faults of this kind and in particular for differentiating between different kinds of faults must thus be able to distinguish between light rays, or beams, which leave the strip at different angles.

In a specially advantageous fashion the invention can be used in apparatus for determining surface faults in sheet metal. In this connection the laser beam is directed inclined towards the sheet metal and light reflected from the metal surface is gathered by a cylindrical lens which is preferably arranged astride the angle of normal specular reflection parallel to the direction of scanning. The apparatus can, however, also operate in transmission especially for the investigation of foils or textiles. In this case a corresponding cylindrical lens is preferably located in the extension of the sharply defined light beam which illuminates the strip from one side. Faults in the strip then give rise to characteristic angular deflections and/or scattering of the light beam in solid angle ranges characteristic of the nature of the fault.

Especially important is the detection both of scratches on metal surfaces and also of large area dents or bumps on the surface. In each case, however, the fault determining apparatus in accordance with the invention usefully has, in addition, a receiving channel which operates by remission and which in known manner responds to defects which influence the remitted light. A receiving channel of this kind can also be provided to the side of the main beam for recognizing defects during the through-illumination of foils. This channel can operate both with remitted light and also with scattered transmitted light. For textiles an additional defect recognition channel of this kind operates by remission.

Optical apparatus has already become known from DE-AS No. 25 32 603 for the detection of light leaving the surface of a strip at different angles. This apparatus, however, requires a light conducting rod of rectangular cross-section and of relatively high optical quality as the light conduction in the light conducting rod must be so exactly carried out so that the original angular relationship between the light beams leaving the scanning bead and passing to the detector are fully preserved.

A significantly lower optical quality can be accepted for the light conducting rod if this is not used to differentiate between the different angles at which light leaves a surface but rather is only used to pass light sent in another manner from a specified angular range onto its surface by total reflection to a photodetector arranged at one or both end faces of the light conducting rod. An apparatus of this kind for monitoring a material strip for the location of faults is known from DE-OS No. 24 33 683. This known apparatus, however, only makes it possible to distinguish between two angular ranges lying in a specified plane.

A completely new type of light conducting rod has become known from DE-OS No. 25 08 366, this light conducting rod is provided at its side diametrically opposite to the light entry surface region with a narrow stepped mirror arrangement which extends in a straight line in the direction of the longitudinal axis of the rod and the individual mirrors of the stepped mirror arrangement are inclined to the longitudinal axis of the light conducting rod in such a way that diametrically incident light is deflected at angles of total reflection into the light conducting rod. It is important in this connection that the light rays extending in a section at right angles to the optical axis do not fall at normal incidence but rather at oblique incidence onto the small plane mirrors in order that, after a single or multiple total reflection, the light rays so far as possible do not impinge for a second time on the stepped mirror arrangement where they would be lost from the further light conduction.

The previously known light conducting rod is of round cross-section and makes it possible to guide the largest part of the received light incident on the surface region to a photodetector provided at one or both end faces. If only one photodetector is arranged at one end face the opposite end face of the light conducting rod is usefully made reflecting. It is also already known to form the individual mirrors of the stepped mirror arrangement with convex curvature transversely to the longitudinal axis in order to improve the scattering effect which improves the homogeneity. Furthermore, several very narrow stepped mirror arrangements can be arranged directly alongside one another.

The new light conducting rod which results in a significantly larger light yield is e.g. used in an optical scanning system, e.g. for investigating a strip of material, in accordance with DE-OS No. 25 50 815, of course in this case a differentiation between different angular ranges of the light leaving the material strip is not possible.

In accordance with an older suggestion for an apparatus for detecting the location of faults on the reflecting surface of a web three light conducting rods of the type known among other things from DE-OS No. 25 08 366 are arranged in parallel alongside one another so that the central light conducting rod is somewhat displaced in the direction of the light beam relative to the two side disposed light conducting rods. By suitably arranged cylindrical lenses the light leaving the surface of the web at different angular ranges is respectively deflected onto only one of the three light conducting rods. The central light conducting rod receives the light leaving the strip at the angle of reflection whilst the two side disposed light conducting rods are normally not illuminated. In a further older suggestion the light leaving the surface of the strip is firstly directed in parallel in a plane via a cylindrical lens and is then guided to a light receiving device by a cylindrical mirror.

Even when it is possible, using the known apparatuses and devices in accordance with the older suggestions, to distinguish between various angular ranges at which light leaves a surface certain difficulties are still associated with distinguishing between, in particular, scratches and dents or large area bumps on metal surfaces. Furthermore it is difficult, with the known optical arrangements, to generate exact straight line scanning lines on the light conducting rods or the forwardly disposed cylindrical lenses.

The object of the present invention thus resides in providing an apparatus for the determination of faults on strip material, which are distinguished by light reflected or transmitted in various directions from the strip, in which the apparatus, by optimum imaging of the scanning region on the light receiving devices and also simple and comprehensible optical construction is particularly well suited for clearly differentiating between different types of faults; especially between scratches on metal surfaces on the one hand and large area dents or depressions on the other hand.

For accomplishing this object there is provided in accordance with a first generalised aspect of the invention apparatus for determining faults in strip material comprising means for projecting light onto the strip for linewise scanning thereof, a first cylindrical lens arranged parallel to the direction of linewise scanning for imaging light from the scanned line on a first cylindrical mirror with its optical axis at right angles to the scanned line, there being further provided first and second detection means for detecting light received from the first cylindrical mirror and wherein the first detection means is arranged to detect light influenced by a fault to deviate within a first plane defined by the scanned line and its image at the first cylindrical mirror and the second detection means is arranged to detect light deviating from said first plane in second planes transverse thereto and to the strip.

In this way the combination of the first cylindrical lens and the first cylindrical mirror produce a spatial separation of the various deviating beams of light within the image field of the first cylindrical mirror which enables the different deviating beams to be conveniently isolated and regrouped for detection purposes.

In accordance with a further aspect of the invention which typifies a useful practical embodiment there is provided apparatus for determining faults in strip material comprising means for generating a scanning light bead on the strip, a first cylindrical lens extending over the scanning region with its focal line extending optically parallel to the direction of movement of the scanning light bead on the strip, first and second strip-like cylindrical mirrors arranged behind the focal line and optically spaced apart from one another by the distance of their focal lengths and with their focal lines optically at right angles to the direction of movement of the scanning light bead on the strip, a second cylindrical lens cooperating with the first and second cylindrical mirrors, and a light receiving device illuminated from the second cylindrical lens and having at least one light conducting rod for receiving light from the second cylindrical lens along a surface region and for transmitting this light to at least one photoelectric converter arranged at an end face of the light conducting rod, the arrangement being such that (a) the first cylindrical lens images the scanning light bead on the first cylindrical mirror;

(b) the first cylindrical mirror reflects the incident light to the second cylindrical lens which is arranged parallel to the first cylindrical lens and spaced from the first cylindrical mirror by its focal length;

(c) a plane mirror is arranged behind the cylindrical lens at least along a part of its length and reflects the incident light through the second cylindrical lens to the second cylindrical mirror; and (d) the second cylindrical lens is passed through twice on account of the arrangement of the plane mirror and images the surface of the first cylindrical mirror on the surface of the second cylindrical mirror.

By means of this construction faults which bring about deflections of the normally reflected or transmitted laser beam in directions at right angles to the scanning direction can be collected at that region of the second cylindrical lens which is not covered by the plane mirror. The relevant types of faults are in particular dents, depressions, bulges or the like. In contrast the light deflected into the scanning direction by other types of faults, in particular scratches, is gathered by the plane mirror arranged behind the second cylindrical lens and is passed via the second cylindrical mirror to the light receiving device where a corresponding electrical signal is likewise generated by using photoelectric converters.

It is especially advantageous if the light receiving device is spaced from the second cylindrical mirror at a distance equal to its focal length. Apart from this the second cylindrical mirror should be arranged spaced by its focal length from the second cylindrical lens. In this manner the normally reflected light or, the light passing through the strip emerges as a moving beam displaced parallel to itself from the second cylindrical mirror and illuminates in this way the light conducting rod or the light conducting rods of the light receiving device at right angles to its axis. This is important as the electrical signal received at the end face of each light conducting rod is attenuated on account of the characteristics of the stepped mirror arrangement if the angle of incidence is larger than 20°.

It is especially advantageous if the two cylindrical mirrors have the same focal length and are constructionally united as a single striplike cylindrical mirror. In accordance with the invention a single striplike cylindrical mirror can thus be used on which the scanning light bead is twice generated via cylindrical lenses at points spaced apart at right angles to its longitudinal axis. The cylindrical mirror can be kept extremely small despite its double utilization in accordance with the invention as the image of the scanning light bead brought about by the cylindrical lenses is a narrow line extending in the longitudinal direction of the striplike cylindrical mirror and, on account of the imaging regimen no broadening of this narrow line occurs even for light deflections at right angles to the scanning direction.

It is especially advantageous if the second cylindrical lens is planoconvex and the plane mirror is formed by a mirror coating of the plane surface. In this way two cylindrical lenses and a plane mirror are constructionally united with one another which has advantages from the point of view of technical manufacture and assembly.

In accordance with a first practical embodiment it can be arranged that the plane mirror extends over the entire second cylindrical lens and that deflecting mirrors are provided at its central region which reflect the incident light in the central region on both sides of the longitudinal axis of the lens to photodetectors. It is, however, preferred if the plane mirror is interrupted in the central region of the second cylindrical lens and that photodetectors are located behind this region. Thus, in this case, special deflecting means are not required. Three photodetectors are preferably arranged alongside each other transverse to the longitudinal axis of the lens.

The central photodetector thus receives the light which is normally reflected at the surface of the strip, or the light passing in a straight line through the strip, whilst the two neighbouring photodetectors are solely intended to receive light if the scanning light bead impinges on a fault which produces a deflection of the incident light at right angles to the scanning direction. Such deflections are brought about by large area bumps or dents on the surface of sheet metal.

Preferably, in this connection, a third cylindrical lens which concentrates the light onto the photodetectors is arranged transverse to and either in front of or behind the second cylindrical lens. The length of the third cylindrical lens is the same as the width of the second cylindrical lens and is common to all three photodetectors.

In accordance with a further advantageous embodiment the light receiving device has three light conducting rods arranged alongside one another and if necessary somewhat displaced in the direction of the light beam. A receiving cylindrical lens is arranged in front of each light conducting rod which, together with the preferably round light conducting rod, concentrates the light beam onto the stepped mirror arrangement. The three receiving cylindrical lenses should in this connection be preferably cut in longitudinal direction from a single planoconvex cylindrical lens and the two outer lenses then reversed and arranged near the central piece. In this way the outer ray paths are deflected somewhat outwardly so that the associated light conducting rods are better spaced from the central light conducting rod.

The sequence in which the individual optical elements are arranged in a plane in right angles to the scanning direction is of some importance. Preferably the first image of the scanning light bead, the second cylindrical lens, the second image of the scanning light bead and the light receiving device are arranged one after another in a specific direction in a plane at right angles to the scanning direction.

The invention is intended to extend to embodiments of the kind in which the beam paths are folded between at least some of the individual optical elements by striplike plane mirrors. In this way an optimum spatial arrangement of the individual optical components is achieved and in all a very compact easily mountable and easily accessible apparatus is provided.

A constructionally especially advantageous realization of the subject of the invention is characterized in that the cylindrical mirror is arranged essentially over the first cylindrical lens and two deflecting mirrors are arranged between the first cylindrical lens and the cylindrical mirror as a result of which the beam path is displaced sideways in the necessary and desired manner.

Both the cylindrical lens and also the light receiving device can be arranged at the top due to the beam folding by means of plane mirrors.

It is particularly advantageous if the light conducting rods used are of the type incorporating stepped mirror arrangements as this ensures an efficient collection of the available light.

The invention will now be described in the following by way of example and with reference to the drawings in which are shown.

Figure 1:
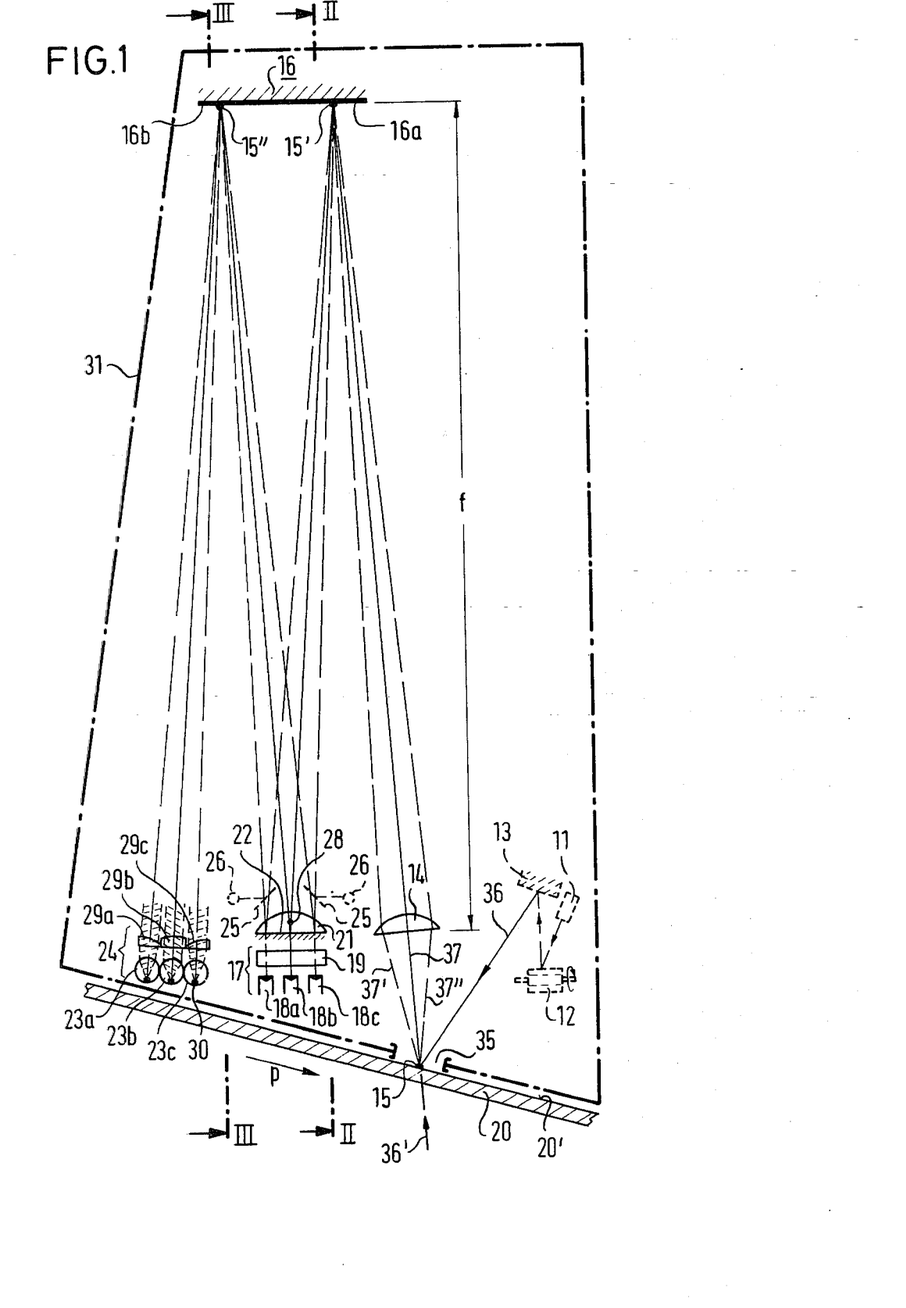
FIG. 1 a schematic illustration of the basic construction of a fault detecting apparatus in accordance with the invention in a section at right angles to the scanning direction, FIG. 2 a schematic view on the line II—II of FIG. 1, FIG. 3 a schematic view on the line III—III of FIG. 1, FIG. 4 an enlarged section of FIG. 1 in the region of the second cylindrical lens, FIG. 5 a schematic section from FIG. 1 in the region of the light receiving device operating with light conducting rods, FIG. 6 a section on the line VI—VI through a light conducting rod used in accordance with the invention, FIG. 7 a schematic sectional view in a plane at right angles to the scanning direction of a fault detection apparatus similar to that shown in FIG. 1 with a multiply folded beam path for providing a compact constructional arrangement, FIG. 8 a view analogous to the views of FIGS. 1 and 7 of a further possible embodiment and FIG. 9 a view analogous to the views of FIGS. 1, 7 and 8 of a further embodiment of a fault detecting apparatus in accordance with the invention.

As seen in FIG. 1 the apparatus for the detection of faults in accordance with the invention is located in a housing 31 indicated in chain-dotted lines which has an opening 35 at the lower end. The opening 35 extends in a direction at right angles to the plane of the drawing over the entire width of a strip of material 20 which is continuously moved beneath the housing 31 in the direction of the arrow p. As can be seen from FIGS. 1 and 2 the opening 35 is of slitlike construction.

Figure 2:
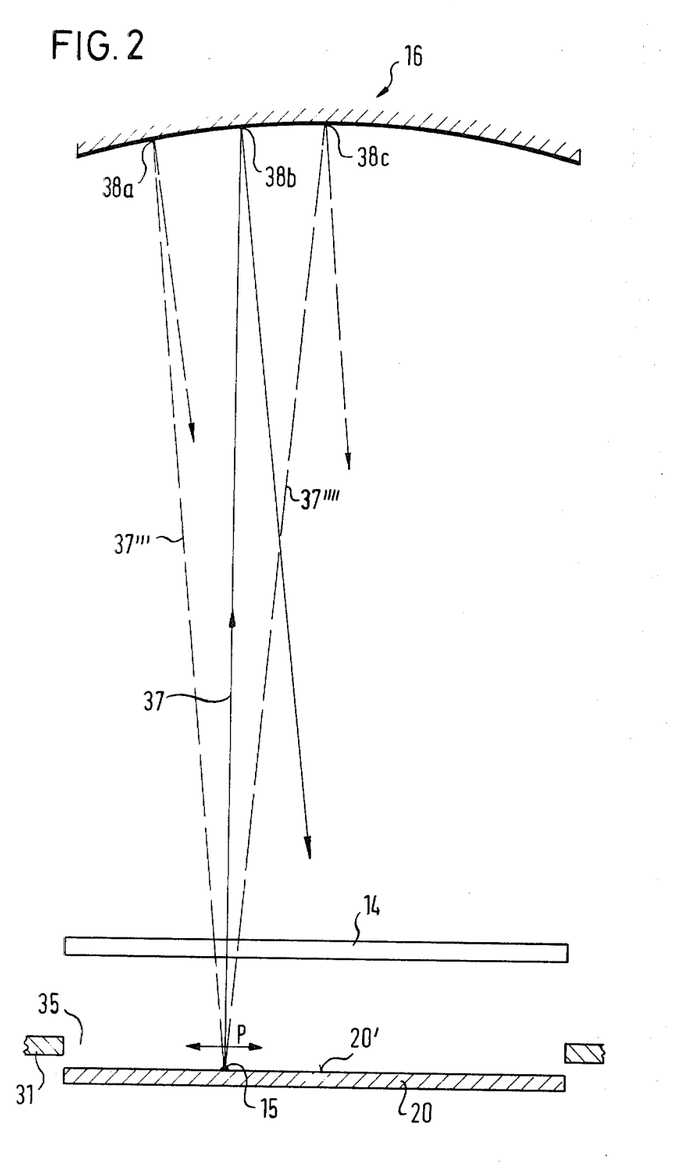

A scanning light bead 15 is generated by a sharply defined laser beam 36 on the surface of the strip 20 facing the housing 31. This scanning light bead executes as seen in FIG. 2 a periodic scanning movement in the direction of the double arrow P over the surface of the strip 20. In FIG. 1 the scanning direction P is at right angles to the plane of the drawing.

The sharply defined laser scanning beam 36 which generates the scanning light bead 15 should move parallel to itself in a direction at right angles to the plane of FIG. 1 in order to bring about the scanning procedure. This can e.g. be achieved in the known manner by a laser light source arrangement 11, a continuously rotating mirror wheel 12 and a strip-like concave mirror 13 extending at right angles to the plane of FIG. 1.

If the apparatus is intended to operate with transmitted light then the scanning ray generating arrangement should be arranged on the opposite side of the strip 20. The scanning ray 36' which results in this way is shown in broken lines in FIG. 1. The following description, however, assumes that the strip 20 is of sheet metal the surface 20' of which should be investigated for faults.

The scanning ray 36 does not impinge at right angles but rather obliquely on the surface 20' of the sheet metal 20 and is reflected at the angle of reflection to a first cylindrical lens 14 which, in accordance with FIGS. 1 and 2, extends parallel to the strip 20 and to the slit opening 35 in the scanning direction P. For customary sheet metal surfaces the reflection of the scanning beam 36 does not solely result in the main beam 37 arranged at the angle of reflection but rather also at other scattering angles distributed about the main beam 37. There is thus no exact angle of reflection but rather a reflection lobe centered in the direction of the main beam 37.

The focal length of the cylindrical lens 14 is so chosen that it images the scanning light bead 15 in the plane of FIG. 1 at 15' on the surface of a first cylindrical mirror 16a. The cylindrical mirror 16a extends optically directly at right angles to the cylindrical lens 14 so that in the plane of FIG. 1 it solely has the effect of a plane reflector.

It can be seen from FIG. 2 that the cylindrical lens 14 has no refractive effect in the plane of FIG. 2 but rather only the cylindrical mirror 16a.

The beams shown in broken lines in the FIGS. 1 and 2 are intended to signify deflections of the main reflected beam 37 in all four directions which can be brought about by the faults on the surface 20' of the strip 20. FIG. 1 shows that the deflections occurring in the plane of FIG. 1 do not affect the generation at 15' of a narrow line with the width of the image of the scanning light bead 15 on account of the characteristics of the cylindrical lens 14.

Deflections of the main beam 37 in the plane of FIG. 2 at right angles to FIG. 1 result, however, in the light received from the cylindrical lens 14 impinging at different positions 38a, b or 38c on the cylindrical mirror 16a.

Figure 3:
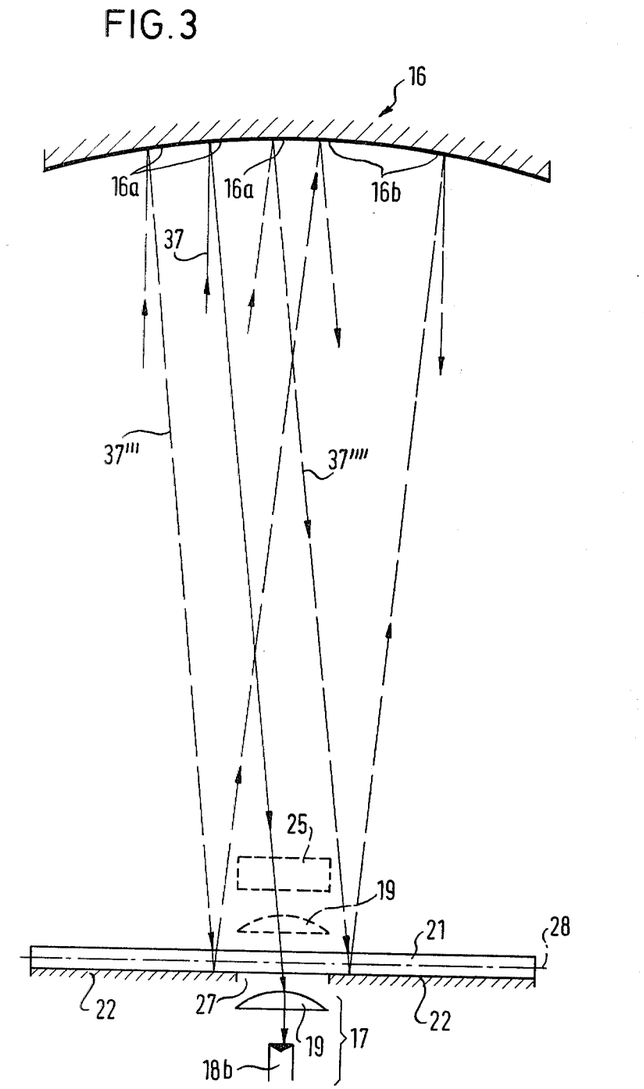

As shown in FIGS. 1 and 3 the light impinging on the cylindrical mirror 16a is reflected to a second cylindrical lens 21 arranged alongside the first cylindrical lens 14. The second cylindrical lens 21 at its side remote from the cylindrical mirror 16a is made flat and, apart from a central region 27, is provided with a mirror surface 22 on its flat side. The cylindrical lens 21 thus works like a cylindrical lens with a plane mirror arranged behind it.

The longitudinal axis 28 of the second cylindrical lens 21 likewise extends optically in the scanning direction P, i.e. the axes of the cylindrical lenses 14 and 21 extend parallel to one another.

The light beams reflected from the first cylindrical mirror 16a to the cylindrical lens 21 are, in accordance with FIG. 1 and to the extent that they impinge on the plane mirror surface 22, reflected to a further cylindrical mirror 16b so that they pass twice through the cylindrical lens 21. The focal length of the cylindrical lens 21 is so chosen that it images in the plane of FIG. 1 the image 15' of the scanning light bead 15 at 15" on the surface of the second cylindrical mirror 16b.

The cylindrical axis of the cylindrical mirror 16b extends parallel to the axis of the cylindrical mirror 16a and thus at right angles to the longitudinal axes of the cylindrical lenses 14, 21. In the preferred embodiment of FIGS. 1 to 3 the two cylindrical mirrors 16a, 16b have the same focal length f and are constructionally united to a single striplike cylindrical mirror 16.

Figure 4:
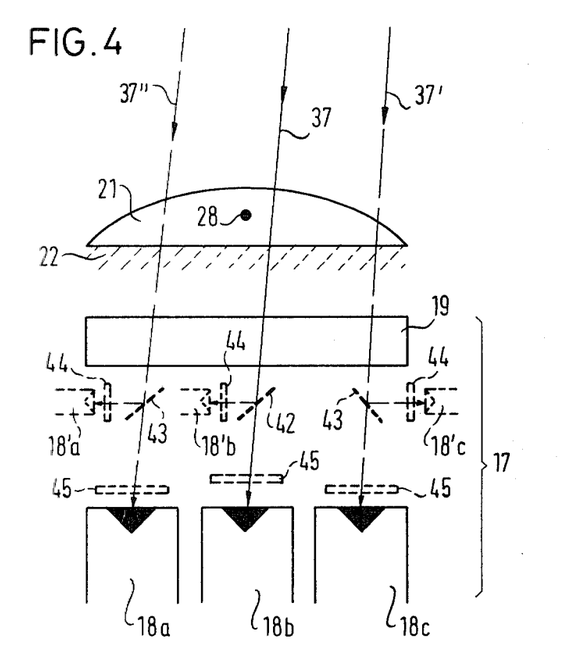

As can be seen particularly clearly from FIGS. 1, 3 and 4 the transmitting central region 27 of the cylindrical lens 21 is so arranged that the light of the reflected main beam which leaves the surface 20' at the angle of reflection, and which as seen in FIG. 2 impinges on the cylindrical mirror 16 parallel to the optical axis thereof, reaches the centre of the central range 27 of the cylindrical lens 21 where the focal line of the cylindrical mirror 16 is located.

Directly behind and arranged at right angles to the second cylindrical lens 21, there is located a third cylindrical lens 19 the length of which is the same as the width of the cylindrical lens 21 and the width of which, in accordance with FIG. 3, corresponds to the width of the light transmitting central region 27.

In accordance with FIG. 3 the further cylindrical lens 19 concentrates light incident thereon onto three photodetectors 18a, b, c which are arranged alongside one another as seen in FIGS. 1 and 4 and which are preferably formed as photomultipliers. The cylindrical lens 19 and the photodetector 18 together form a photoelectric converter arrangement 17 for determining large area dents and bumps on the surface 20' of the sheet metal 20.

If a fault on the surface 20' does not deflect the light in the plane of FIG. 2 but, however, in the plane of FIG. 1 the deflected side beams 37' or 37" reach the photodetectors 18a, 18c. Thus light deflections characteristic of the kind for dents and impressions on sheet metal surfaces can be detected for measurement by an electrical signal at the output of these photodetectors. For this purpose the photodetectors 18a, b and c can be connected to a suitable electronic processing circuit.

A further possibility for detection and measurement of deflected beams 37', 37" is signified in FIG. 1 at 25 and 26. Plane deflection mirrors 25 can be attached above the second cylindrical lens 21 in the central region 27 which deflect the side light beams 37', 37" to photodetectors 26.

If, however, deflections of the main beam 37 are also produced in the plane of FIG. 2 by other types of fault (e.g. scratches) then the deflected rays or beams 37''' and 37'''' as seen in FIG. 3 no longer reach the central range 27 but impinge on the mirror surfaces 22 on each side of the central region 27. In this way the light beams 37''' and 37'''' are reflected in the manner shown in FIG. 1 to the cylindrical mirror 16b where they once more generate a line image of the scanning light bead 15. When dimensioning the cylindrical lens 21 it must in any case be borne in mind that the light beams reaching the cylindrical mirror 16b pass twice through the cylindrical lens 21.

On account of the arrangement in accordance with the invention the light rays reflected at the cylindrical mirror 16b leave this mirror practically parallel to the light beam entering the cylindrical mirror 16a. The consequence is that the light impinges substantially at right angles onto the light receiving device 24 which is arranged alongside the cylindrical lenses 14, 21 and comprises three light conducting rods 23a, b, c arranged alongside one another and cylindrical lenses 29a, b and c (see also FIG. 5) arranged in front of the light conducting rods. The cylindrical lenses 29a, b and c are cut out of a single planoconvex cylindrical lens and the two outer parts are then arranged reversed in the manner shown in FIGS. 1 and 5. In this way an outward deflection of the beam path is achieved so that the light conducting rods 23a, b and c can be arranged at a somewhat larger distance from one another.

Figure 5:
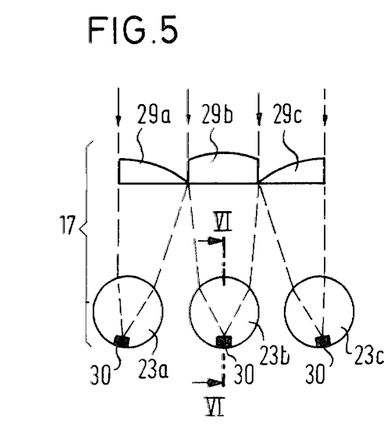
Figure 6:
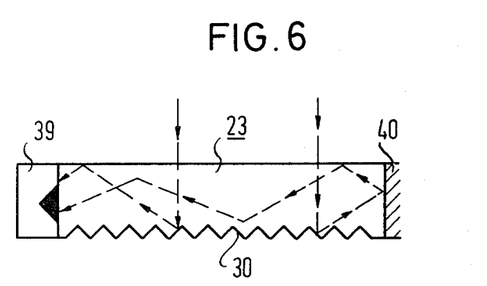

As seen in FIGS. 5 and 6 the light conducting rods are provided with a stepped mirror arrangement 30 at their surface regions remote from the light entry side. The stepped mirror arrangement 30 ensures, in the manner shown in FIG. 6, that incident light at right angles to the rod axis is reflected at angles of total reflection into the rod. In this way the light reaches a photodetector 39 or a mirror surface 40 at the opposite end face. The light is once more reflected back from this mirror surface 40 into the rod 30 and likewise reaches the light detector 39 after repeated total reflections.

On account of the arrangement in accordance with the invention the light to be measured impinges on the light conducting rods 23 at angles which only deviate slightly from the perpendicular which is important for a troublefree outcome to the measurement.

Photodetectors are arranged at one or both end faces of each light conducting rod 23a, b and c, which are likewise connected to the same electronic processing circuit as that to which the photodetectors 18 are also applied.

In the simplest case the processing electronic circuit solely indicates at which of the photodetectors 18 or 39 an electrical signal arises which exceeds a specified threshold.

As was already explained above electrical signals appear exclusively at the photodetectors 18a, b and c only if deflections of the main beam 37 only occur in the plane of FIG. 1, not, however, in the plane of FIG. 2.

If deflections are present in the plane of FIG. 2 (37''', 37'''') then either the central photodetector 18b or the photodetector 39 attached to the central light conducting 23b, receives light and releases a corresponding electrical signal. Such deflections are characteristic of scratches on the sheet metal surface. A superposition of the two basic deflections results also in electrical signals at the photodetectors 39 of the two outer light conducting rods 23a, 23c.

FIG. 3 also indicates the further possibility of arranging the cylindrical lens 19 in front of the second cylindrical lens 21 as shown in broken lines.

Figure 7:
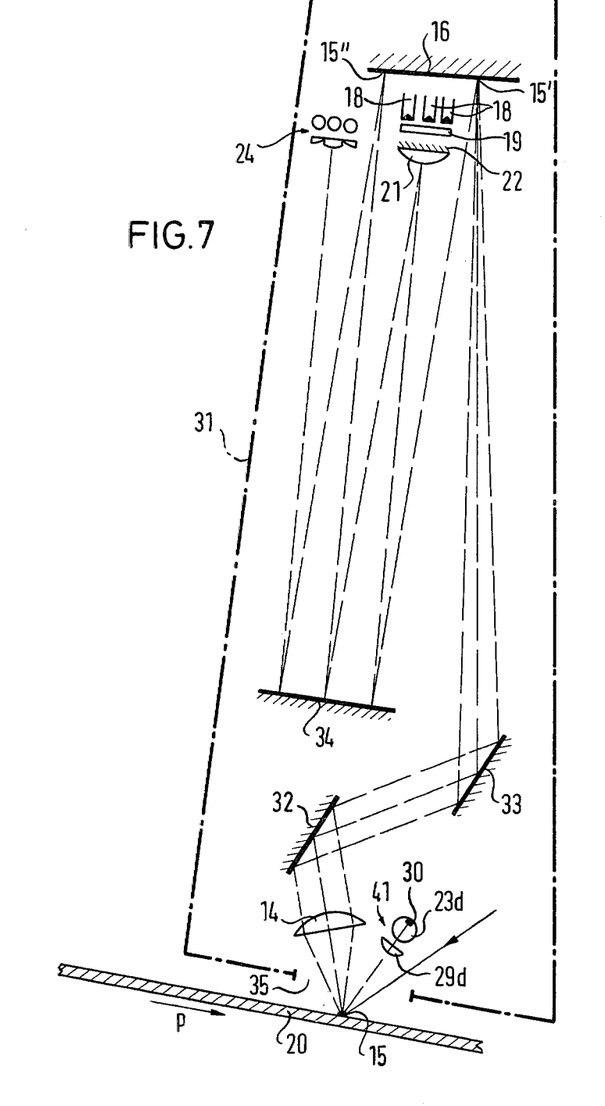

FIG. 7 shows an arrangement which is optically identical to the arrangement of FIG. 1 but in which the individual beam paths are folded by plane mirrors 32, 33, 34 in the manner seen in FIG. 7 for the purpose of achieving a compact construction. First of all the light beam leaving the cylindrical lens 14 is deflected by a deflecting mirror 32 to a further plane mirror 33 displaced from and arranged parallel to the deflecting mirror 32 and which subsequently directs the light beam upwardly to the cylindrical mirror 16. On account of this displacement of the beam the cylindrical mirror 16 can be arranged practically over the scanning slot 35 and, indeed, at the top end of the housing.

The further plane mirror 34 has a triple function and could also be divided into three individual plane mirrors. The plane mirror 34 makes it possible for the second cylindrical lens 21 with the photodetectors 18 and the light receiving device 24 to be housed in the upper region of the housing 31. As the electrical connections must also be provided at this position and if necessary electrical amplifying and processing devices must also be housed it is useful to arrange these parts as far away from the scanning slit 35 as possible.

A receiving device 41 for remitted light is also schematically illustrated in FIG. 7. The receiving device 41 comprises a cylindrical lens 29d extending parallel to the cylindrical lens 14 and a further light conducting rod 23d with stepped mirror arrangement 30. One or two photodetectors arranged at the end face or the end faces of the light conducting rod 23d then produce an electrical signal which indicates defects on the surface of the strip 20.

Figure 8:
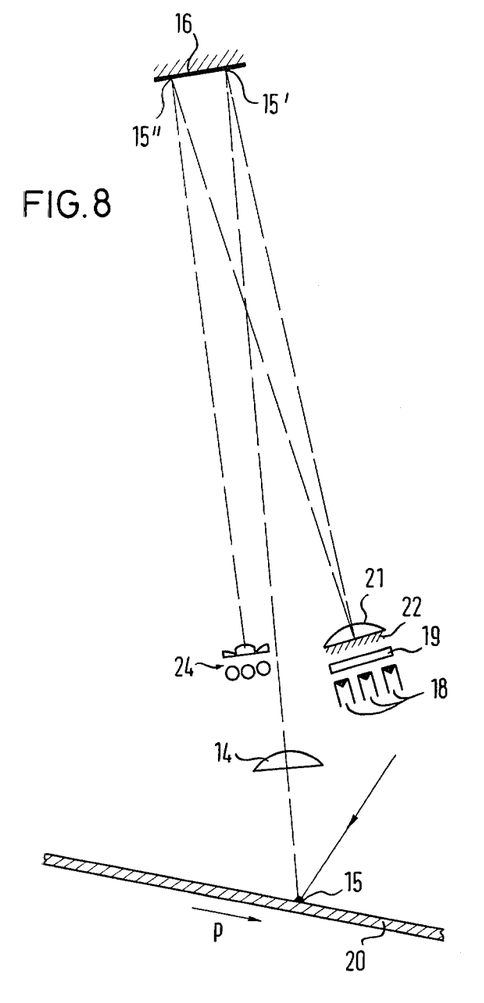

FIG. 8 shows a further possibility for the guidance of the beam path. In FIG. 8 the light beam which produces the image 15' is firstly reflected away from the second image of the light bead 15" to the correspondingly arranged second cylindrical lens 21 which then, however, projects the light beam once more onto the opposite side of the image 15' at the position 15". The light receiving device 24 is provided beneath this position 15".

Figure 9:
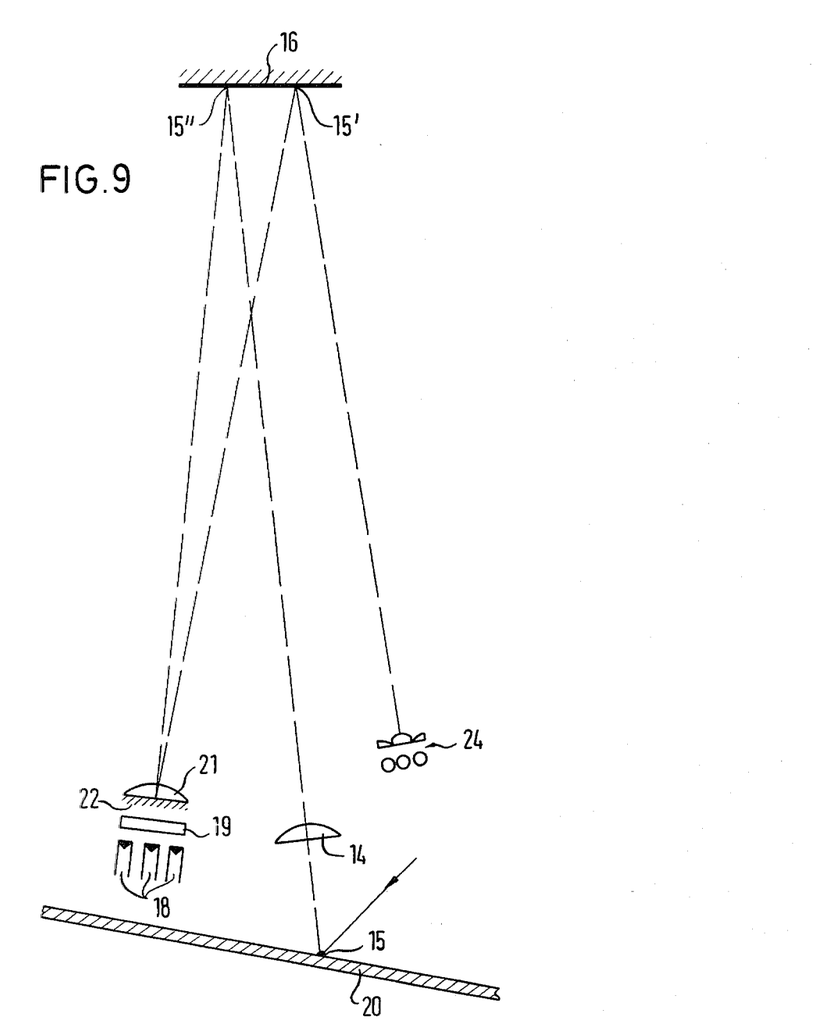

In the embodiment of FIG. 9 the conditions are reversed in the form of a mirror image which, as for the exemplary embodiment of FIG. 8, likewise leads to a usable solution.

A particularly straight line movement of the scanning point at all scanned optical elements is, however, achieved by the preferred embodiment of FIGS. 1 to 7.

The non-mirrored central region of the plane mirror 22 is of such a width that the extent of the light bead generated from the light source is located directly inside the interrupted mirror region when the surface of the strip is truly reflecting and also if necessary on taking into account the trivial tiltings that can take place during the transport movement of the strip. In this manner the main light is not reflected to the three light conducting rods so that light scattered by faults in particular scratches can be determined with significantly higher sensitivity. The unmirrored region of the plane mirror 22 should thus not keep the light scattered by distortions of the surface away from the three light conducting rods 23.

In FIG. 4 is also shown in broken lines how the apparatus in accordance with the invention can be further modified for the recognition of colour faults on the surface of the strip or in transparent strip material.

As seen in FIG. 4 a ray divider 42 is selectively arranged in front of a photodetector 18b and divides off a portion of the main light and passes it via a red filter 44 to a further photodetector 18'b. A blue filter 45 is arranged in front of the central photodetector 18b. The basic underlying inventive thought of this embodiment is to be seen in that light, for an exactly reflecting surface of the strip or which passes undisturbed through a transparent strip, is divided after its passage through the unmirrored region into two or more colour channels the output channels of which are then passed to a suitable electronic processing circuit which carries out the recognition of colour faults.

In the deflected light rays 37', 37" which extend to the sides of the main light beam 37 there can likewise be provided, in accordance with FIG. 4, beam dividers 43 which divide the relevant light beams once more into two partial beams which either illuminate the photodetectors 18'a, 18'c via red filters 44 or photodetectors 18a, 18c via blue filters 45. Thus the side beams can also be divided into two or more colour channels so that coloured dentlike bumps or depressions in the surface or striations in foils can be recognized.

The photodetectors 18 are preferably photomultipliers.

Whilst the specification and claims talk of cylindrical mirrors and lenses it will be understood that this is a broad term which covers also mirrors and lenses having sections other than circular e.g. conic sections such as parabolic. Furthermore, whilst the specific embodiments are all directed to linewise scanning using a light bead from a scanning beam it will be understood that the term "linewise scanning" also includes scanning a line at a time using a light curtain to illuminate the strip a line at a line rather than point by point along a line. The above described apparatus is clearly operable in this way providing a sufficient intensity of light is available.

It will be appreciated by those skilled in the art that many modifications can be made to the specific arrangements disclosed herein without departing from the scope of the present teaching as herein described and claimed.

I claim:

1. Apparatus for determining faults in a strip of material comprising means for projecting light onto the strip for linewise scanning thereof, a first cylindrical lens arranged parallel to the direction of linewise scanning for imaging light from the scanned line on a first cylindrical mirror having its optical axis at a right angle to the scanned line, first and second detection means for detecting light received from the first cylindrical mirror and wherein the first detection means is arranged to detect light influenced by a fault to deviate within a first plane defined by the scanned line and its image at the first cylindrical mirror and wherein the second detection means is arranged to detect light deviating from said first plane in second planes transverse thereto and to the strip.

2. Apparatus for determining faults in a strip of material comprising means for generating a scanning light bead on the strip, a first cylindrical lens extending over the scanning region with its focal line extending optically parallel to the direction of movement of the scanning light bead on the strip, first and second strip-like cylindrical mirrors arranged behind the focal line and optically spaced apart from one another by the distance of their focal lengths and with their focal lines optically at right angles to the direction of movement of the scanning light bead on the strip, a second cylindrical lens cooperating with the first and second cylindrical mirrors, and a light receiving device illuminated from the second cylindrical lens and having at least one light conducting rod for receiving light from the second cylindrical lens along a surface region and for transmitting this light to at least one photoelectric converter arranged at an end face of the light conducting rod the arrangement being such that:
    (a) the first cylindrical lens images the scanning light bead on the first cylindrical mirror;
    (b) the first cylindrical mirror reflects the incident light to the second cylindrical lens which is arranged parallel to the first cylindrical lens and spaced from the first cylindrical mirror by its focal length;
    (c) a plane mirror is arranged behind the cylindrical lens at least along a part of its length and reflects the incident light through the second cylindrical lens to the second cylindrical mirror; and
    (d) the second cylindrical lens is passed through twice on account of the arrangement of the plane mirror and images the surface of the first cylindrical mirror on the surface of the second cylindrical mirror.

3. Apparatus according to claim 2 wherein the light receiving device is arranged spaced from the second cylindrical mirror at a distance equal to its focal length.

4. Apparatus according to claim 2 wherein the second cylindrical mirror is spaced by its focal length from the second cylindrical lens.

5. Apparatus according to claim 2 wherein the first and second cylindrical mirrors have the same focal length.

6. Apparatus according to claim 5 wherein the first and second cylindrical mirrors are constructionally united to a single strip-like cylindrical mirror.

7. Apparatus according to claim 2 wherein the second cylindrical lens is plano-convex and the plane mirror is formed by making the plane surface reflecting.

8. Apparatus according to claim 2 wherein the plane mirror extends over the entire second cylindrical lens, and including deflecting mirrors located in a central region of the plane mirror which reflect the light incident in the central region on both sides of the longitudinal axis of the second cylindrical lens to photodetectors.

9. Apparatus according to claim 2 wherein the plane mirror is interrupted in a central region of the second cylindrical lens and wherein photodetectors are located behind this region.

10. Appartus according to claim 9 wherein first, second and third photodetectors are arranged alongside one another transverse to the longitudinal axis of the second cylindrical lens.

11. Apparatus according to claim 10 wherein a third cylindrical lens concentrating the light on the photodetector is arranged transverse to and a relatively short distance from one of the optically upstream or downstream side of the second cylindrical lens.

12. Apparatus according to claim 2 wherein the light receiving device comprises first, second and third light conducting rods arranged alongside one another.

13. Apparatus according to claim 12 wherein a receiving cylindrical lens is arranged in front of each light conducting rod and together with the light conducting rod concentrates the light beam on a stepped mirror arrangement.

14. Apparatus according to claim 13 wherein the receiving cylindrical lenses are cut in the longitudinal direction out of a single planoconvex cylinder lens into a middle piece and first and second outer pieces, and wherein the outer pieces are reversed and arranged near the middle piece.

15. Apparatus according to claim 2 wherein the first image of the scanning light bead, the second cylindrical lens, the second image of the scanning light bead and the light receiving device are arranged one after the other in a specific direction in a plane at a right angle to the scanning direction.

16. Apparatus according to claim 2 wherein the beam paths between at least some of the individual optical elements are folded by strip-like plane mirrors.

17. Apparatus according to claim 16 wherein the first and second cylindrical mirrors are united to form a single cylindrical mirror arranged substantially over the first cylindrical lens and first and second plane mirrors are arranged between the first cylindrical lens and the cylindrical mirror.

18. Apparatus according to claim 16 wherein both the second cylidnrical lens and also the light receiving device are arranged upwardly.

* * * * *